United States Patent [19]

Witholt et al.

[11] Patent Number: 5,344,769
[45] Date of Patent: Sep. 6, 1994

[54] MICROBIOLOGICAL PRODUCTION OF POLYESTERS

[75] Inventors: Bernard Witholt, Paterswolde; Gerrit Eggink, Ede; Gjalt W. Huisman, Groningen, all of Netherlands

[73] Assignee: Rijksuniversiteit te Groningen, Netherlands

[21] Appl. No.: 773,891

[22] PCT Filed: Apr. 3, 1990

[86] PCT No.: PCT/NL90/00041

§ 371 Date: Oct. 24, 1991

§ 102(e) Date: Oct. 24, 1991

[87] PCT Pub. No.: WO90/12104

PCT Pub. Date: Oct. 18, 1990

[30] Foreign Application Priority Data

Apr. 4, 1989 [NL] Netherlands .......................... 8900827

[51] Int. Cl.$^5$ .......................... C12P 7/62; C12P 7/44; C12P 7/42; C08G 63/06
[52] U.S. Cl. .................................. 435/135; 435/142; 435/146; 435/280; 435/874; 435/875; 435/876; 435/877
[58] Field of Search ............... 435/135, 142, 146, 280, 435/874–877; 528/361, 354

[56] References Cited

U.S. PATENT DOCUMENTS

| | | | |
|---|---|---|---|
| 4,477,654 | 10/1984 | Holmes et al. | 528/361 |
| 5,135,859 | 8/1992 | Witholt et al. | 435/135 |
| 5,149,644 | 9/1992 | Lubitz | 435/146 |
| 5,191,016 | 3/1993 | Yalpani | 528/361 |

OTHER PUBLICATIONS

Huisman et al., "Synthesis of Poly-3-Hydroxyalkanoates Is a Common Feature of Fluorescent Pseudomonads", Applied & Environmental Microbiology, Aug. 1989, pp. 1949–1954.

*Primary Examiner*—Herbert J. Lilling

[57] ABSTRACT

The invention relates to a microbiological process for the production of polyesters and utilizes bacteria of the *Pseudomanas fluorescens* rRNA branch according to the phylogenetic classification of De Vos and De Ley. These bacteria are cultured under aerobic fermentation conditions in a nutrient medium comprising an excess of at least one assimilarable acylic aliphatic hydrocarbon compound having 6–18 carbon atoms and a limiting quantity of at least one of other nutrients essential for growth to form poly-3-hydroxyalkanaoates.

17 Claims, No Drawings

MICROBIOLOGICAL PRODUCTION OF POLYESTERS

This invention relates to a process for producing polyesters by aerobically culturing microorganisms, preferably with nutrient limitation. More in particular, the invention relates to a process for producing polyesters by culturing Pseudomonas bacteria under aerobic conditions in a nutrient medium preferably containing an excess of a carbon source and a limiting quantity of at least one of the other nutrients essential for growth, the carbon source comprising at least one assimilable acyclic aliphatic hydrocarbon compound, and, if desired, recovering the biopolymer formed from the cells.

Such a process is known from European patent application EP-A-0 274 151. According to the process described therein *Pseudomonas oleovorans* bacteria are used which surprisingly proved capable of converting hydrocarbon compounds with certain nutrient limitations into polymeric products. The polymers formed were found to differ from the known PHB, i.e. poly(3-hydroxy-butyrate). It turned out that they were built up from units having the formula (1): —CO—CH$_2$—CH [(CH$_2$)$_m$CH$_3$]—O—, and/or units having the formula (2): —CO—CH$_2$—CH [(CH$_2$)$_{m-1}$CH=CH$_2$]—O—, in which m is an integer of 2–8. The composition of the biopolymers formed by the bacteria [which will hereinafter be referred to as PHA, i.e. poly(3-hydroxy-alkanoate)] proved dependent on the nature of the hydrocarbon compound present in the medium. When, e.g., the substrate used was n-decane, the polymer formed proved to consist of 3-hydroxy-decanoate, 3-hydroxy-octanoate and 3-hydroxy-hexanoate units. On the other hand, when the substrate used was n-undecane, the polymer formed proved to consist of 3-hydroxy-undecanoate, 3-hydroxy-nonanoate and 3-hydroxy-heptanoate units. When the substrate used was an unsaturated hydrocarbon compound (1-olefins, such as 1-octene), the polymer formed also comprised units of formula (2).

Surprisingly, it has now been found that bacterial species other than *Pseudomonas oleovorans* can be used as well, namely bacteria belonging to the pseudomonads of the *Pseudomonas fluorescens* rRNA branch according to the phylogenetic classification by de Vos and de Ley, Int. J. of Syst. Bacteriol. 33, 1983, 487–509. According to this classification, different Pseudomonas branches can be distinguished in ribosomal RNA by homology, namely the rRNA branch of *Pseudomonas solanacearum*, the rRNA branch of *Pseudomonas acidovorans* and the rRNA branch of *Pseudomonas fluorescens*. The bacteria belonging to the two first branches are found to be PHB formers, while the bacteria belonging to the last-mentioned branch have in con, non that on certain carbon sources (not on sugars, methanol or short fatty acids) they form no PHB but PHA's, especially with nutrient limitation (starvation).

PHB-forming pseudomonads of the rRNA branch of *Pseudomonas solanacearum* are *P. solanacearum, P. cepacia, P. marginata, P. caryophili* and *P. lemoignei*. PHB-forming pseudomonads of the rRNA branch of *Pseudomonas acidovorans* are *P. acidovorans, P. delafieldii, P. testosteroni, P. facilis, P. palleronii* and *P. flava*. Pseudomonads of the rRNA branch of *Pseudomonas fluorescens* forming no PHB but PHA are *P. fluorescens*, biotype I (inter alia the prototype), *P. fluorescens* of biotype II, *P. fluorescens* of biotype III, *P. fluorescens* of biotype IV (such as *P. lemonnieri*), *P. putida* biotype A (which, inter alia, includes *P. oleovorans*), *P. putida* biotype B, *P. aureofaciens, P. syringae, P. stutzeri, P. mendocina, P. chloraohis, P. cichorii, P. pseudoalcaligenes, P. alcaligenes* and *P. aeruginosa*. The pseudomonads of the *Pseudomonas fluorescens* rRNA branch according to the phylogenetic classification by de Vos and de Ley in Int. J. of Syst. Bacteriol. 33, 1983, 487–509, correspond to the pseudomonads from group I according to the determination in Bergey's Manual of Determinative Bacteriology.

When selecting the substrate, it must be considered that bacterial species of the *Pseudomonas fluorescens* rRNA branch other than *Pseudomonas oleovorans* are mostly incapable of metabolizing paraffins. The ability of *P. oleovorans* to metabolize paraffins is due to plasmid-encoded (OCT plasmid) enzymes which are involved in the first steps of the paraffin oxidation. On the other hand, paraffin oxidation products, such as alkanols, alkanals, paraffin carboxylic acids and paraffin dicarboxylic acids, can often be metabolized by these other bacterial species. Also, the length of the hydrocarbon compound serving as a substrate preferred by a selected bacterial species may be different from the length preferred by *P. oleovorans*. While in case of bacteria of the species *P. oleovorans* the best results are obtained by using C$_6$–C$_{12}$ paraffins and alkanols or C$_6$–C$_{18}$ (un)saturated fatty acids as a substrate, it is better in case of *P. aeruginosa* bacteria to use C$_{12}$–C$_{16}$ paraffins and alkanols or C$_6$–C$_{10}$ paraffin dicarboxylic acids.

In the first place, the invention therefore provides a process for producing polyesters by culturing bacteria of the *Pseudomonas fluorescens* rRNA branch according to the phylogenetic classification by de Vos and de Ley in Int. J. of Syst. Bacteriol 33, 1983, 487–509, with the exception of *Pseudomonas oleovorans*, under aerobic conditions in a nutrient medium comprising as a carbon source at least one assimilable acyclic aliphatic hydrocarbon compound, and, if desired, recovering the biopolymer formed from the cells.

The invention particularly provides a process for producing polyesters by culturing bacteria of the *Pseudomonas fluorescens* rRNA branch according to the phylogenetic classification by de Vos and de Ley in Int. J. of Syst. Bacteriol. 33, 1983, 487–509, with the exception of *Pseudomonas oleovorans*, under aerobic conditions in a nutrient medium comprising an excess of a carbon source and a limiting quantity of at least one of the other nutrients essential for growth, the carbon source comprising at least one assimilable acyclic aliphatic hydrocarbon compound, and, if desired, recovering the biopolymer formed from the cells.

More in particular, the invention provides such a process, which comprises the use of bacteria selected from the group consisting of

*Pseudomonas fluorescens*, biotype I
*Pseudomonas fluorescens*, biotype II
*Pseudomonas fluorescens*, biotype III
*Pseudomonas fluorescens*, biotype IV
*Pseudomonas putida* biotype A (except *P. oleovorans*)
*Pseudomonas putida* biotype B
*Pseudomonas aureofaciens*
*Pseudomonas syringae*
*Pseudomonas stutzeri*
*Pseudomonas mendocina*
*Pseudomonas chloraphis*
*Pseudomonas cichorii*
*Pseudomonas pseudoalcaligenes*

*Pseudomonas alcaligenes*
*Pseudomonas aeruginosa.*

In the process according to the invention a saturated or unsaturated paraffin or paraffin oxidation product having 6 or more carbon atoms is generally used as the assimilable acyclic aliphatic hydrocarbon compound. More in particular, the substrate used is a saturated or unsaturated paraffin or paraffin oxidation product having 6–24 carbon atoms, preferably 6–18 carbon atoms. The term "paraffin oxidation product" as used herein particularly means alkanols, alkanals, alkanoic acids and paraffin dicarboxylic acids occurring as intermediates in the natural paraffin decomposition. Of course, steps must be taken, if necessary, to avoid any toxic effect of such substances. For this reason, when the substrates used are, e.g., alkanols or alkanals, an inert auxiliary phase, such as dibutyl phthalate, will usually be added to the medium for the purpose of dilution. Preferably, however, the substrate used is a paraffin carboxylic acid having 6–18, preferably 12–16 carbon atoms, or a paraffin dicarboxylic acid having 6–18, preferably 6–12 carbon atoms. If desired, there is also used a reactant, such as Brij 58, to keep these substrates in solution.

The composition of the polymers obtained by the process according to the invention depends on the substrate used. When a substrate having an even number of carbon atoms is used, the units constituting the polymer also have an even number of carbon atoms. Similarly, the polymer units have an odd number of carbon atoms when a substrate having an odd number of carbon atoms is used. The smallest polymer units have 6 and 7 carbon atoms, respectively. However, also when substrates having more than 12 carbon atoms are used, the polymers formed essentially do not contain units having more than 12 carbon atoms. In practice, the units having 8 and 9 carbon atoms, respectively, are always found to be predominant.

In order to stimulate the bacteria to form PHA, a nutrient limitation is preferably used, i.e. in practice, the aerobic cultivation is carried out with a nitrogen, phosphorus, sulfur or magnesium limitation, preferably on a medium, such as an E2-medium, with a nitrogen limitation. The growth and polymer forming conditions are essentially as described in European patent application EP-A-0 274 151. According to these commonly used conditions the aerobic cultivation is carried out (fed batchwise or continuously) at pH 5–9, preferably 7, at a temperature below 37° C., preferably about 30° C., and with adequate agitation at a dissolved oxygen tension above 30%, preferably about 50% or more saturation with air. If desired, a system with two liquid phases is used, one of which is an aqueous phase containing the water-soluble nutrients and the bacteria, and the other of which is an apolar phase containing the hydrocarbon compound(s) serving as a substrate. However, when more polar substrates are used, such as the mono- and dicarboxylic acids, the system preferred will be a one-phase system using suitable surfactants.

In practice, the procedure will be commonly such that the aerobic cultivation with nutrient limitation is preceded by an exponential growth phase without nutrient limitations until a cell density of at least 2 g/l is reached. It is also possible, however, to have a co-metabolic process taken place, in which a preferably inexpensive carbon source, such as glucose, sucrose, molasses etc., is used for growth (i.e. for multiplying cell mass) and a paraffin or paraffin oxidation product is used as a substrate for the desired polymer formation.

The stationary phase, in which the biopolymer inclusions are formed, is preferably not continued too long, because, after reaching a maximum, the polymer content is again decreased. Preferably, therefore, the biopolymer containing cells formed in the stationary phase with nutrient limitation are harvested before a significant decrease of the biopolymer content of the cells has taken place.

However, it has been established by way of experiment that PHA's can also be formed under non-limiting conditions. Thus, bacteria of the strain *Pseudomonas putida* KT2442 were found to form PHA during the entire fermentation, both during the exponential and during the stationary phase. The use of growth-limiting conditions is therefore not necessary.

The biopolymer included in the cells need not necessarily be isolated, because the bacterial cells with the biopolymer inclusions therein can sometimes be directly used, as proposed, e.g., in U.S. Pat. No. 3,107,172. For most uses, however, isolation and purification of the polymer will be desirable or necessary. For this purpose, many known per se methods can be used. The bacterial cells can be broken up in many ways which are well known to those skilled in the art, e.g., by using shear forces (by means of homogenizers, grinders, so-called "French press" and the like), by carrying out an osmotic shock treatment, by using sonorous or ultrasonorous vibrations, by enzymatic cell wall decomposition, or by spray drying the cell suspension. Subsequently, the polymer can be separated from the other components in many known per se manners, including solvent extraction and centrifugation. One suitable method of isolation described in the above European patent application EP-A-0 274 151 uses isopycnic centrifugation. For isolation on a larger scale it is preferable for the biopolymer to be isolated by converting the harvested cells into spheroplasts, breaking these up by a treatment with sonorous vibrations, separating and, if desired, washing and drying the top layer formed after centrifugation. Preferably, the conversion into spheroplasts is effected in the presence of sucrose. Centrifugation proceeds satisfactorily if effected for about 30 minutes at 10,000 g. The polymer then forms a white top layer on the supernatant and can easily be separated. Contaminations can be removed by washing, after which the washed polymer is brought into a suitable dry form, preferably by freeze drying.

Another suitable procedure for the isolation of the polymer formed is the procedure described in European patent application EP-A-0 274 151. When compared with the biochemical procedure using a sucrose gradient and different centrifugation steps, extraction of freeze dried cells with, e.g., chloroform is easier, faster, and conducive to a higher yield of a purer product.

For the uses of the polyesters formed reference is made to the above European patent application EP-A-0 274 151, including the possibility of chemically modifying the resulting biopolymers or crosslinking them with other polymer chains, and the use for the manufacture of products, such as sutures, films, skin or bone grafts etc.

The invention also provides a process for producing optically active carboxylic acids or carboxylic acid esters, which comprises hydrolyzing a polyester obtained by the process according to the invention, and, if desired, esterifying the resulting monomers. It is often not easy to obtain such optically active compounds, which may have utility, e.g., as intermediates in the manufacture of pharmaceutical products, or for research, in an optically pure form by chemical means. If, as a result of the substrate used, the process produces mixtures of different monomers, these can, if desired, be separated in a known per se manner.

The invention is illustrated in and by the following experimental section.

(1) Bacterial Strains and Growth Conditions

The strains listed in Table A were used. The growth media used were E-medium (Vogel and Bonner, J. Biol. Chem. 218, 1956, 97–106), E2-medium (Lageveen et al, Appl. Env. Microbiol. 54, 1988, 2924–2932) or 0.5xE2.

E-medium has the following composition:

| E-medium has the following composition: | |
|---|---|
| trisodium citrate | 2.0 g/l |
| $MgSO_4 \cdot 7H_2O$ | 0.2 g/l |
| $NaNH_4HPO_4 \cdot 4H_2O$ | 3.5 g/l |
| $K_2HPO_4$ | 10 g/l |
| 1000 MT | 1 ml/l |
| E2-medium has the following composition: | |
| $NaNH_4HPO_4 \cdot 4H_2O$ | 3.5 g/l |
| $K_2HPO_4 \cdot 3H_2O$ | 7.5 g/l |
| $KH_2PO_4$ | 3.7 g/l |
| 1000 MT | 1 ml/l |
| 100 mM $MgSO_4$ | 10 ml/l |
| 0.5 × E2-medium has the following composition: | |
| $NaNH_4HPO_4 \cdot 4H_2O$ | 3.5 g/l |
| $K_2HPO_4 \cdot 3H_2O$ | 3.8 g/l |
| $KH_2PO_4$ | 1.9 g/l |
| 1000 MT | 1 ml/l |
| 100 mM $MgSO_4$ | 10 ml/l |
| 1000 MT (in 1 N HCl) has the following composition: | |
| $FeSO_4 \cdot 7H_2O$ | 2.78 g/l |
| $MnCl_2 \cdot 4H_2O$ | 1.98 g/l |
| $CoSO_4 \cdot 7H_2O$ | 2.81 g/l |
| $CaCl_2 \cdot 2H_2O$ | 1.47 g/l |
| $CuCl_2 \cdot 2H_2O$ | 0.17 g/l |
| $ZnSO_4 \cdot 7H_2O$ | 0.29 g/l |

The above media allow growth up to a certain cell density, after which nitrogen is limiting. The cell density obtainable on the 0.5xE2-medium is expected to be about 0.7–0.9 mg/ml. at this cell density nitrogen is limiting, and further increase in cell mass is the result of an accumulation of PHA.

The fatty acids were dissolved in 10% Brij 58 up to final concentrations of 10 mM (for butyrate, valerate, octanoate, nonanoate, decanoate and undecanoate), 5 mM (for laurate, tridecanoate, myristate, pentadecanoate, oleate, elaidate and γ-linolate) and 2 mM (for palmirate, heptadecanoate, stearate and erucate) as 10 times more concentrated stock solutions, brought to pH 7.0 by adding 1N KOH, and sterilized through a filter (Jenkins and Nunn, J. Bacteriol. 169, 1987, 42–52). 3-Hydroxy-butyrate was added up to 0.7%. 1-Octanol and octanal (3% v/v) were added directly to liquid cultures and, in vapor form, to cells growing on solid media. To 1-octanol or octanal containing liquid cultures were added 17% dibutyl phthalate to prevent damage to the cells.

TABLE A

| strain | strains used characteristics | reference |
|---|---|---|
| *P. oleovorans* | | |
| GPo1 | OCT | (a) |
| GPo12 | OCT⁻ | Kok, thesis |
| Groningen | | |
| *P. putida* | | |

TABLE A-continued

| strain | strains used characteristics | reference |
|---|---|---|
| PpG1 | | (b) |
| KT2442 | TOL⁻, Rf^r | (c) |
| *P. aeruginosa* | | |
| PA01 | prototype | (d) |
| *P. fluorescens* | prototype | (e), DSM 50090 |
| *P. lemonnieri* | | (e), DSM 50415 |
| *P. testosteroni* | prototype | (f) | abbreviations:
OCT: OCT plasmid;
TOL: TOL plasmid;
Rf^r: rifampicin resistance;
DSM: Deutsche Sammlung für Mikroorganismen und Zellkulturen GmbH, Braunschweig, FRG.
(a): Schwartz and McCoy, Appl. Microbiol., 1973, 217–218
(b): Grund et al, J. Bacteriol., 1975, 546–556
(c): Bagdasarian et al, Gene, 1981, 237–247
(d): Holloway, Bacter. Rev. 3, 1969, 419–443
(e): Stanier et al, J. Gen. Microbiol., 1966, 159–271
(f): Marcus and Talalay, J. Biol. Chem., 1956, 661–674

(2) Determination of PHA

For a qualitative analysis of the presence of PHA the cells were examined microscopically. For a quantitative analysis the cells were cultured on 0.5xE2 agar plates or in 50 ml 0.5xE2 cultures and tested for the presence and composition of PHA according to the method described before by Lageveen et al. The composition of the polymers was also determined at isolated polymer obtained from 1 l cultures after chloroform extraction.

For the polymer test, cells were harvested, lyophilized and then treated with 15% sulfuric acid in methanol/chloroform at 100° C for 140 min. to convert fatty acids into the methyl esters. The methyl esters were then analyzed by means of gas-liquid chromatography (GLC). The measurement of methyl-3-hydroxybutyrate was adapted by starting the GLC program at 68° C. After 2 min. at this temperature the column was heated for 20 min. at a rate of 5° C./min. Then the column temperature was increased to 278° C. at a rate of 10° C./min. to remove all the high-molecular components. On the basis of the cell density (Witholt, J. Bacteriol. 109, 1972, 350–364) and the peak surface ratios of the monomers and the internal standard (methyl benzoate) the amount of polymer accumulated by the cells and the composition thereof could be determined.

(3) Formation of PHA by *P. oleovorans* on paraffin oxidation products

The formation of PHA by the prototype of paraffin oxidizing pseudomonads, namely *P. oleovorans* GPo1, using 1-octanol, octanal or octanoate as a substrate, was examined. These carbon sources were added to final amounts of 3% (vol/vol) or 10 mM (octanoate). Because 1-octanol and octanal were toxic to the cells, the cultures were supplemented with 17% dibutyl phthalate. The results are listed in Table B.

When 1-octanol or octanoate was used as a substrate, PHA was actually formed. When octanal was used as a substrate, no growth occurred. The yield of polymer was highest after growth on octanoate. The polymers formed consisted mainly of 3-hydroxy-octanoate units (90%), and the rest consisted of 3-hydroxy-hexanoate units. This corresponds to the results obtained using octane.

TABLE B

| | effect of oxidation state of substrate | | | |
|---|---|---|---|---|
| substrate | dry cell mass (mg/ml) | cellular PHA content (%) | polymer composition 30H-6 | 30H-8 |
| 1-octanol | 1.3 | 3.1 | 0.10 | 0.90 |
| octanal | no growth | | | |
| octanoate | 1.2 | 8.7 | 0.12 | 0.88 |

Bacteria of the strain P. oleovorans GPo1 were grown in 50 ml 0.5xE2 medium on the substrates referred to and analyzed after 20 hours of growth on PHA. The cellular PHA content is the percentage of polymer mass relative to the dry cell mass. By 30H-6 and 30H-8 are meant 3-hydroxy-hexanoate and 3-hydroxyoctanoate, respectively.

(4) Formation of PHA by Other Pseudomonads

Not only for bacteria of the strain P. oleovorans GPo1, but also for the strains P. oleovorans GPo12 (an OCT-derivative of GPo1), P. putida PpG1 (a plasmid-less strain isolated from soil), and P. putida KT2442 (a rifampicin-resistant strain derived from P. putida mt-2 and stripped of the TOL plasmid), which strains do not grow on paraffins, was polymer formation examined. All these strains belong to the group of P. putida, biotype A. The strains were grown on agar plates with minimum medium on octanol vapor and analyzed microscopically for the presence of PHA. In all these strains the formation of a reserve material was established from the intracellular accumulation of polymer granules observed in phase contrast microscopy as transparent (white) dots.

In order to determine the amount and composition of the reserve material, cells of the plates were collected and analyzed for PHA. As appears from Table C, the tested strains, except P. putida PpG1, produced PHA, in which 90% consisted of 3-hydroxy-octanoate and 10% of 3-hydroxy-hexanoate. The strain P. putida PpG1 also produced PHA, but this was found to be nearly a homopolymer, because no less than 96% thereof was built up from C8 and only 4% from C6 monomers. As compared with the P. oleovorans strains GPo1 and GPo12, the P. putida strains PpG1 and KT2442 proved to accumulate higher intracellular PHA contents.

TABLE C

| | PHA synthesis by other Pseudomonas strains | |
|---|---|---|
| strain (%) | Cellular PHA content (%) | fraction 30H-6 |
| GPo1 | 2–5 | 9.5 ± 1.0 |
| GPo12 | 2–5 | 9.4 ± 1.5 |
| PpG1 | 10–20 | 4.0 ± 0.7 |
| KT2442 | 10–20 | 9.0 ± 1.1 |

The strains were grown on 1-octanol on 0.5xE2 plates. The composition is shown by means of the fraction 3-hydroxy-hexanoate monomers in the polyester, and the rest is formed by 3-hydroxy-octanoate.

(5) Formation of PHA by yet other Pseudomonads

There are different classifications of pseudomonads, such as the classification according to rRNA homology (de Vos and de Ley, Int. J. Syst. Bacteriol. 33, 1983, 487–509), according to similarities between enzymes involved in the biosynthesis of aromatic amino acids (Byng et al, J. Mol. Evol. 19, 1983, 272–282), and according to metabolism properties as described in Bergey's Manual of Determinative Bacteriology. In all these different classification systems the fluorescent Pseudomonas strains (the species P. putida, P. aeruginosa and P. fluorescens) are members of the same group and have in common that they are incapable of forming PHB.

The investigation into the formation of PHA's was continued for different Pseudomonas strains from the P. fluorescens rRNA branch, namely the prototypes P. aeruginosa PAO, P. fluorescens and P. lemonnieri as well as the above-mentioned P. oleovorans and P. putida strains and further the species P. testosteroni not belonging to this group. All these strains were grown on 10 mM octanoate or on 0.7% 3-hydroxy-butyrate in 50 ml 0.5xE2 cultures. The cells were harvested, and PHA was determined at whole cells (Table D).

The P. putida strains were also grown in E2-medium on 30 mM octanoate or 0.7% 3-hydroxy-butyrate in 1 l fermenters, followed by isolation of the polyesters. The composition of the polymers was found to correspond to the composition determined in the analysis at whole cells. The PHA's of cells grown on octanoate always consisted of 3-hydroxy-hexanoate, 3-hydroxy-octanoate, and small amounts of 3-hydroxy-decanoate. No 3-hydroxy fatty acids having an odd number of carbon atoms were detected. After growth on 3-hydroxy-butyrate, 3-hydroxy fatty acids were not found in culture samples, nor in the material obtained by precipitation of a chloroform extract of the whole cells.

Bacteria of the species P. aeruginosa, P. fluorescens and P. lemonnieri were all found to form PHA after growth on octanoate, while they formed no polymer during growth on 3-hydroxy-butyrate. On the other hand, P. testosteroni, which was incapable of growing on octanoate, was found to form PHB during growth on 3-hydroxy-butyrate or decanoate. During growth on the latter substrate only 13% of the monomers did not consist of 3-hydroxy-butyrate. The amounts of PHA formed by the different species were widely divergent.

The P. putida and P. oleovorans strains gave 30–50% PHA, P. aeruginosa gave about 15%, and P. fluorescens, the prototype of the fluorescent pseudomonads, gave only 1–2% PHA. On the other hand, the species P. lemonnieri belonging to P. fluorescens Biotype IV accumulated PHA up to nearly 40% of its dry cell mass. These percentages, however, only serve as a general indication of the PHA forming capacity of the optionally fluorescent pseudomonads of the P. fluorescens rRNA branch, because the culture conditions may have an effect on the PHA yield and the PHA synthesis is not yet optimized by the different strains.

TABLE D

| | PHA formation by different Pseudomonas strains | | | | | |
|---|---|---|---|---|---|---|
| strain | substrate | polymer content | composition 30H-4 | 30H-6 | 30H-8 | 30H-10 |
| P. oleovorans | | | | | | |
| GPo1 | HB | 0 | | | | |
| | oct | 29.7 | — | 0.07 | 0.90 | 0.03 |
| GPo12 | HB | 0 | | | | |
| | oct | 34.1 | — | 0.06 | 0.91 | 0.03 |
| P. putida | | | | | | |
| PpG1 | HB | 0 | | | | |
| | oct | 29.4 | — | 0.03 | 0.93 | 0.04 |
| KT2442 | HB | 0 | | | | |
| | oct | 47.1 | — | 0.08 | 0.91 | 0.01 |
| P. aeruginosa | | | | | | |
| PAO | HB | 0.1 | — | — | — | 1.0 |
| | oct | 14.4 | — | 0.08 | 0.86 | 0.07 |

TABLE D-continued

| | PHA formation by different Pseudomonas strains | | | | | |
|---|---|---|---|---|---|---|
| strain | sub-strate | polymer content | composition | | | |
| | | | 3OH-4 | 3OH-6 | 3OH-8 | 3OH-10 |
| P. fluorescens | | | | | | |
| | HB | 0.4 | — | — | — | 1.0 |
| | oct | 1.6 | — | 0.14 | 0.63 | 0.22 |
| P. lemonneri | | | | | | |
| DSM 50415 | HB | 0.7 | — | — | 0.14 | 0.86 |
| | oct | 38.5 | — | 0.06 | 0.91 | 0.03 |
| P. testosteroni | | | | | | |
| | HB | 15.4 | 0.99 | — | — | 0.01 |
| | oct | no growth | | | | |
| | dec | 6.0 | 0.87 | 0.03 | 0.09 | 0.02 |

The abbreviations used for the substrate are: HB: 3-hydroxy-butyrate; oct: octanoate; and dec: decanoate.

(6) Effect of the Substrate on the PHA Formation

In order to determine the effect of the growth substrate on the composition of the polymer formed, P. oleovorans GPo1 was cultured in 50 ml cultures containing 0.5xE2-medium supplemented with a fatty acid having 4–22 carbon atoms, after which the cells were harvested and tested for the presence of poly-3-hydroxy-alkanoates. The results are listed in Table E.

The PHA formation was limited when small fatty acids, such as 3-hydroxy-butyrate, butyrate and valerate, were used. Despite the limited production (less than 1.5%) the PHA's formed contained $C_8$, $C_{10}$ and $C_{12}$ monomers. Monomers having less than 8 carbon atoms were not observed.

When carboxylic acids of medium length, such as octanoate, nonanoate, decanoate and undecanoate, were used, a substantial polymer formation took place (more than 8%). The composition of the polyesters corresponded to that of the PHA's formed during growth on the corresponding n-paraffins.

Growth on longer fatty acids also led to PHA synthesis. When laurate, tridecanoate, myristate, pentadecanoate, and palmirate were used as a carbon source, the amount of polymer formed was in the same range as had been found during use of fatty acids of medium length (more than 5%). When longer saturated fatty acids, such as heptadecanoate and stearate, were used, the bacteria did not grow satisfactorily, and no polymer formation was detected. On the other hand, during use of unsaturated carboxylic acids having 18 carbon atoms, growth and polymer formation took place. This was not the case when erucate, an unsaturated fatty acid having 22 carbon atoms was used.

When a substrate having more than 12 carbon atoms (laurate and higher) was used, the composition of the polyesters was found to be not so substrate-dependent anymore: when the substrate had an even number of carbon atoms, 3-hydroxy-dodecanoate was always the largest monomer, and when the substrate had an odd number of carbon atoms, 3-hydroxy-undecanoate was always the largest monomer. The composition of the PHA's formed on longer (12 and more carbon atoms) fatty acids having an even number of carbon atoms showed a fixed ratio for the $C_6$, $C_8$, $C_{10}$ and $C_{12}$ monomers of about 1.3:8.9:4.7:1. The composition of the PHA's formed on longer (11 and more carbon atoms) fatty acids having an odd number of carbon atoms showed a fixed ratio for the $C_7$, $C_9$ and $C_{11}$ monomers of about 2.3:3.4:1.

TABLE 3

| | PHA formation by P. oleovorans on $C_4$-$C_{22}$ fatty acids | | | | | | | |
|---|---|---|---|---|---|---|---|---|
| sub-strate | polymer-content (%) | polymer composition | | | | | | |
| | | 3OH-6 | 3OH-7 | 3OH-8 | 3OH-9 | 3OH-10 | 3OH-11 | 3OH-12 |
| saturated fatty acids | | | | | | | | |
| HB | 1.2 | — | — | 0.22 | — | 0.57 | — | 0.21 |
| C4 | 0.6 | — | — | — | — | 0.33 | — | 0.67 |
| C5 | 0.7 | — | — | — | — | 0.35 | — | 0.65 |
| C8 | 8.7 | 0.08 | — | 0.91 | — | 0.01 | — | — |
| C9 | 9.1 | — | 0.35 | — | 0.65 | — | — | — |
| C10 | 12.5 | 0.08 | — | 0.75 | — | 0.17 | — | — |
| C11 | 9.8 | — | 0.28 | — | 0.59 | — | 0.13 | — |
| C12 | 6.6 | 0.06 | — | 0.57 | — | 0.32 | — | 0.05 |
| C13 | 5.4 | — | 0.32 | — | 0.48 | 0.05 | 0.14 | — |
| C14 | 10.6 | 0.07 | — | 0.59 | — | 0.30 | — | 0.04 |
| C15 | 5.3 | — | 0.32 | — | 0.47 | 0.08 | 0.13 | — |
| C16 | 3.4 | 0.08 | — | 0.50 | — | 0.30 | — | 0.12 |
| C17 and C18 | | | | no growth | | | | |
| unsaturated fatty acids | | | | | | | | |
| ole | 7.4 | 0.09 | — | 0.57 | — | 0.28 | — | 0.06 |
| ela | 11.2 | 0.10 | — | 0.56 | — | 0.27 | — | 0.07 |
| lin | 5.9 | 0.10 | — | 0.57 | — | 0.30 | — | 0.04 |
| eru | | | | no growth | | | | |

The abbreviations used for the substrates are: HB: 3-hydroxy-butyrate; C4: butyrate; C5: valerate; C8 to C18: octanoate to octadecanoate; ole: oleate (cis-9-octadecenoate); ela: elaidate (trans-9-octadecenoate); lin: γ-linolenate (cis-6,9,12-octadecatrienoate); eru: erucate (cis-13-docosenoate).

By "—" is indicated: <0.005.

We claim:

1. A process for producing poly-3-hydroxyalkanoates composed of repeating units having 6–10 carbon atoms comprising selecting bacteria from the Pseudomonks fluorescens rRNA branch and culturing said bacteria according to the phylogenetic classification by de Vos and de Ley in Int. J. of Syst. Bacteriol. 33, 1983, 487–509, with the exception of Pseudomonas oleovorans, under aerobic conditions in a nutrient medium comprising an excess of a carbon source and a limiting quantity of at least one of the other nutrients essential for growth, said carbon source comprising at least one assimilable acyclic aliphatic oxidated hydrocarbon compound having 6–18 carbon atoms.

2. A process according to claim 1, in which bacteria are used selected from the group consisting of
*Pseudomonas fluorescens*
*Pseudomonas lemonnieri*
*Pseudomonas putida* biotype A (except *P. oleovorans*)
*Pseudomonas aeruginosa*.

3. A process according to claim 1, in which the assimilable acyclic aliphatic hydrocarbon compound used is a saturated or unsaturated $C_{6-18}$ paraffin oxidation product.

4. A process according to claim 3, in which a paraffin carboxylic acid having 6–18 carbon atoms is used.

5. A process according to claim 4, in which a paraffin carboxylic acid having 12–16 carbon atoms is used.

6. A process according to claim 1, in which the aerobic cultivation is carried out with nitrogen, phosphorus, sulfur or magnesium limitation.

7. A process according to claim 1, in which the aerobic cultivation is carried out at pH 5–9, at a temperature below 37° C., and with adequate agitation at a dissolved oxygen tension above 30%, saturation with air.

8. A process according to claim 1, in which the aerobic cultivation with nutrient limitation is preceded by an exponential growth phase without nutrient limitations until a cell density of at least 2 g/l is reached.

9. The process of claim 1, further comprising recovering the biopolymer formed from the cells.

10. A process according to claim 9, in which the biopolymer containing cells formed in the stationary phase with nutrient limitation are harvested before a significant decrease of the biopolymer content of the cells has taken place.

11. A process according to claim 9, in which the biopolymer is isolated by converting the harvested cells into spheroplasts, breaking these up by a treatment with sonorous vibrations, separating and, if desired, washing and drying the top layer formed after centrifugation, or isolating the biopolymer by solvent extraction.

12. A process according to claim 9, in which the resulting biopolymer is isolated and is then chemically modified by at least one further chemical reaction.

13. A process for producing optically active carboxylic acids or carboxylic acid esters, which comprises the steps of producing poly-3-hydroxyalkanoates composed of repeating units having 6–10 carbon atoms by the process according to claim 1, hydrolyzing the poly-3-hydroxyalkanoates obtained and, if desired, esterifying the resulting monomers.

14. The process of claim 6, wherein the aerobic cultivation is carried out with nitrogen limitation.

15. The process of claim 7, wherein the aerobic cultivation is carried out at about pH 7.

16. The process of claim 7, wherein the aerobic cultivation is carried out at a temperature of about 30° C.

17. The process of claim 7, wherein the aerobic cultivation is carried out at a dissolved oxygen tension of about 50% or more saturation with air.

* * * * *